United States Patent
Nakasuji et al.

(10) Patent No.: US 7,244,933 B2
(45) Date of Patent: Jul. 17, 2007

(54) ELECTRON BEAM APPARATUS, A PATTERN EVALUATION METHOD AND A DEVICE MANUFACTURING METHOD USING THE ELECTRON BEAM APPARATUS OR PATTERN EVALUATION METHOD

(75) Inventors: Mamoru Nakasuji, Kanagawa-ken (JP); Takao Kato, Tokyo (JP); Toshifumi Kimba, Kanagawa-ken (JP); Tohru Satake, Kanagawa-ken (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 11/319,648

(22) Filed: Dec. 29, 2005

(65) Prior Publication Data

US 2006/0102838 A1    May 18, 2006

Related U.S. Application Data

(62) Division of application No. 10/850,432, filed on May 21, 2004, now Pat. No. 7,012,251.

(30) Foreign Application Priority Data

| May 22, 2003 | (JP) | .............................. 2003-144689 |
| Jun. 6, 2003 | (JP) | .............................. 2003-161601 |

(51) Int. Cl.
  *H01J 37/28* (2006.01)
(52) U.S. Cl. .................. 250/307; 250/310; 250/492.22
(58) Field of Classification Search ..................... None
  See application file for complete search history.

(56) References Cited

U.S. PATENT DOCUMENTS

| 6,313,476 | B1 | 11/2001 | Shimizu et al. |
| 6,509,569 | B1 | 1/2003 | Frosien |
| 6,593,152 | B2 | 7/2003 | Nakasuji et al. |
| 6,864,482 | B2 * | 3/2005 | Sato et al. .................. 250/310 |

FOREIGN PATENT DOCUMENTS

JP    7-249393    9/1995

* cited by examiner

*Primary Examiner*—Jack I. Berman
*Assistant Examiner*—Zia R. Hashmi
(74) *Attorney, Agent, or Firm*—Westerman, Hattori, Daniels & Adrian, LLP.

(57) ABSTRACT

Provided is an electron beam apparatus in which an electron beam emitted from an electron gun is separated by a plurality of apertures, images of said apertures are reduced in more than two stages to form multi-beams on a sample surface and to scan said sample thereby, and secondary electrons from said sample are passed through an objective lens, where distances between said secondary electrons are extended, further through an E×B separator, where said secondary electrons are separated from the primary beam, and finally onto secondary electron detectors, where said secondary electrons are detected, wherein a lens defined in the second step for reducing said image of the aperture is composed of two stage lens and an enlarged image of the secondary electron is formed on a position between a first and a second lenses of said two stage lens, thereby reducing an aberration of the optical system for detecting the secondary electrons and allowing as many multi-beams as possible to be formed in the vicinity of a single optical axis.

10 Claims, 9 Drawing Sheets

(a)

(b)

ELECTRON BEAM APPARATUS, A PATTERN EVALUATION METHOD AND A DEVICE MANUFACTURING METHOD USING THE ELECTRON BEAM APPARATUS OR PATTERN EVALUATION METHOD

This application is a divisional of application Ser. No. 10/850,432 filed May 21, 2004 now U.S. Pat. No. 7,012,251.

BACKGROUND OF THE INVENTION

The present invention relates to an apparatus providing a pattern evaluation of a sample, for example, a substrate having a pattern with a minimum line width not greater than 0.1 μm with a high throughput, and also to an evaluation method of a pattern by using the same apparatus.

The present invention further relates to a pattern evaluation method that provides an evaluation, such as a defect inspection for a chip having a pattern with a minimum line width not greater than 0.1 μm in an inexpensive manner, with a reduced foot print as well as with a high throughput.

The present invention further relates to a method for manufacturing a device by using said electron beam apparatus or pattern evaluation method.

In the evaluation of a pattern formed on a substrate by using an electron beam, it has been conventionally suggested to use a multi-beam in order to improve the throughput. Such suggestions may be categorized roughly into two methods: a method of using a multi-beam having a plurality of optical axes; and a method of forming a multi-beam on spots spaced equally from a single optical axis.

The former method, or the method of using the multi-beam having a plurality of optical axes, however, has a problem that a need for making a large number of electron optical lens columns leads to an increase in the entire cost of the apparatus, and a further problem that it is impossible to arrange a large number of optical axes on a single substrate, or on a wafer.

On the other hand, the latter method, or the method of forming the multi-beam on the spots spaced equally from the single optical axis also has a problem that the beam to be formed away from the optical axis increases an aberration in an optical system and does not allow an increase in intensity of the beams. In a trial to address these problems, an attempt to arrange more beams in the locations quite close to the optical axis caused another problem that secondary electrons generated from respective points scanned by the multi-beam overlap with one another due to the aberration in the optical system, while another attempt to extend a space between beams, which allows an individual detection, aiming at preventing the above problem of overlapping, has adversely prohibited producing a large number of multi-beams. Further, the electron beam apparatus according to the prior art typically has a problem that the length of a secondary optical system is rather longer.

More specifically, the apparatus according to the prior art employs a single step of objective lens 4 for focusing a primary electron beam 2 after the beam has passed through a reducing lens 1 onto a sample surface 3, as illustrated in FIG. 10. In an operation of this apparatus, if a landing energy of the primary electrons is large, an excitation voltage of the objective lens 4 will be increased, so that the secondary electrons 5 will form a secondary electron image 6 immediately above the objective lens 4 with a large half-angular aperture αi, as illustrated, which could fall out of lens, unless an aperture size of the lens 8 is made larger. From this point of view, it is necessary to enlarge the aperture size of the lens 8, which in turn, could disadvantageously lead to a drawback of the increased aberration. Further, since a lens of a second optical system is not allowed to be positioned close to the objective lens, the lens having an object point in a distance serving as a magnifying lens, is required to make its image point defined at a further distant location, which disadvantageously makes an entire length of the secondary optical system much longer. It is to be noted that in the drawing, reference numeral 9 designates an E×B separator serving for separating the secondary electrons from the primary optical system.

The present invention has been made in the light of the above problems, and accordingly a first subject to be addressed by the present invention is to provide an electron beam apparatus and an evaluation method of a pattern by using said apparatus, which can be manufactured at low cost and which can reduce the aberration in the optical system for detecting the secondary electrons and to allow the large number of multi-beams to be formed in the vicinity of the single optical axis.

In the art, there has been known a method for providing an evaluation such as a defect inspection for a pattern formed on a chip by using an electron beam apparatus (see, for example, Japanese Patent Laid-open Publication No. Hei7-249393). In the practice according to the prior art, such an evaluation apparatus comprising a memory capable of storing the images for at least two chips is used, wherein an entire pattern formed on a single chip is stored, and said pattern is compared with the entire pattern formed on another chip so as to detect a defect. Further, a probe used for the defect detection is of a type using a single electron beam.

However, the prior art method has a problem that the memory for storing the image data should be extremely large in size and yet a further problem that using only a single beam as the probe results in an extremely low throughput.

Accordingly, a second object of the present invention is to provide a pattern evaluation method that can work effectively with a small sized memory for storing the image data in the evaluation apparatus.

Another object of the present invention is to provide a method which can increase a throughput by using a multi-beam to make the pattern evaluation.

Yet another object of the present invention is to provide a manufacturing method of a device, in which an apparatus or a method as specified above is used to evaluate a sample in the course of processing.

SUMMARY OF THE INVENTION

To solve the first problem defined by the above first object, according to a first aspect of the present invention, there is provided an electron beam apparatus in which an electron beam emitted from an electron gun is separated by a plurality of apertures; images of said apertures are reduced in two steps to form an multi-beam on a sample surface and to scan the sample thereby; and secondary electrons from said sample are passed through an objective lens, where intervals between said secondary electrons are extended, further through an E×B separator, where said secondary electrons are separated from the primary beam, and finally onto a secondary electron detector, where said secondary electrons are detected, said apparatus characterized in that a lens defined in the second step for reducing said images of the apertures is composed of two stage lens and an enlarged image of the secondary electron is formed on an position between a first and a second lens of said two stage lens.

In the above-specified invention, since the objective lens for focusing the primary electron beam onto the sample surface is composed of two stage lens, so that the excitation voltage of the objective lens can be reduced, and thus the secondary electron image can be formed in the position distant from the objective lens, or the image point can be produced on near side of the second lens of the secondary optical system, the aperture size of the secondary optical system may be made small, which is preferable to reduce the aberration. Further, forming the secondary electron image on near side of the second lens of the secondary optical system may eliminate the need to make longer a distance to the image point of the lens, and thereby allow reducing in the length of the secondary optical system.

Further, to solve the first problem defined by the above first object, according to a second aspect of the present invention, there is provided an electron beam apparatus in which an electron beam having passed through a plurality of apertures is reduced by a two stage lens so as to form a multi-beam and to thereby scan a sample; and secondary electrons emanated from said sample are passed through a first lens, where intervals between said secondary electrons are extended, and further through an E×B separator, where said secondary electrons are separated from a primary optical system and are directed into a secondary optical system, where said intervals between said secondary electrons are further extended by at least a lens of one stage, and finally onto a secondary electron detector, where each of said plurality of beams is individually detected, said apparatus characterized in that a deflector for scanning said sample is an electrostatic deflector.

In order to reduce the aberration of the secondary optical system and to form a large number of multi-beams in the vicinity of the single optical axis, it is required that during scanning by the multi-beam, with respect to both in the central region and the peripheral region within the field of scanning, the secondary electrons should enter the first lens of the secondary optical system in a position not so far from the optical axis. If the electromagnetic deflector is employed as the deflector for scanning the sample, in the phase where the primary beam is deflected by that deflector to the left, for example, those returning secondary electrons are deflected to the opposite direction to the primary beam, or to the right, and resultantly the secondary electrons go away from the optical axis and enter the first lens of the secondary optical system in a position far from the optical axis, leading to a greater aberration. However, if the scanning deflector is implemented by the electrostatic deflector as described above, then the secondary electrons are deflected toward the same direction as the primary beam so as to return to the direction of the optical axis and enter the first lens of the secondary optical system in a position close to the optical axis, thereby advantageously reducing the aberration of the secondary optical system.

Further, to solve the first problem defined by the above first object, according to a third aspect of the present invention, there is provided an electron beam apparatus in which an electron beam emitted from an electron gun having a single emission area is entered into a multi-aperture so as to form a multi-beam, said apparatus characterized in that said multi-beam is positioned within a circle having its radius determined from a convergent beam half-angle on the sample and an emittance of said electron gun.

The electron beam apparatus according to the third aspect of the present invention does not require the multi-beam to be positioned on a circle, as typically practiced in the prior art, and so the beams can be formed within said circle with the minimum interval between beams determined to be greater than the resolution of the secondary optical system, which helps advantageously increase the number of beams.

Further, to solve the first problem defined by the above first subject, according to a fourth aspect of the present invention, there is provided a pattern evaluation method for evaluating a pattern formed on a sample comprising:

a.) a step of irradiating an electron beam emitted from an electron gun onto a plurality of apertures;

b.) a step of reducing said electron beams, which have been separated through said apertures, in two or more stages, so as to focus them on a sample and scanning said sample by said reduced electron beams;

c.) a step of extending distances between secondary electrons, which have been emanated from points of scanning on said sample, by an objective lens and separating said secondary electrons from a primary optical system by an E×B separator; and d.) a step of detecting said separated secondary electrons by a secondary electron detector, said method characterized in that the second stage of reducing in said stages for reducing the aperture image is carried out by an objective lens, and a first enlarged image of the secondary electron is formed in a location behind said E×B separator.

Further, to solve the first problem defined by the above first object, according to a fifth aspect of the present invention, there is provided a pattern evaluation method for evaluating a pattern formed on a sample, comprising:

a.) a step of reducing an electron beam, which has passed through a plurality of apertures, by a two stage lens and scanning a sample by said electron beams;

b.) a step of extending intervals between secondary electrons, which have been emanated from points of scanning on said sample, by a first lens;

c.) a step of separating said secondary electrons, after they have passed through said lens, from a first optical system by an E×B separator;

d.) a step of extending intervals between said secondary electrons, after having separated from said primary optical system, by a lens of at least one stage e.) a step of detecting a plurality of secondary electron groups independently by a secondary electron detector; and f.) a step-of forming an image by using said detected signals and performing a pattern evaluation, said method characterized in that said plurality of electron beams are positioned within a circle having a radius determined such that an aberration in the primary optical system or the secondary optical system are controlled to be equal to or less than a predetermined value.

Further, to solve the second problem defined by the above second subject, according to a sixth aspect of the present invention, there is provided a pattern evaluation method for evaluating patterns formed on a plurality of chips on a wafer, comprising:

a.) a step of dividing an area to be evaluated on said wafer into a plurality of stripes, each having a width smaller than a size of a field of view of an electron optical system in an evaluation apparatus and the plurality of stripes being aligned in parallel with one axial direction, wherein assuming that the longitudinal direction of said stripe is defined as Y direction and the transverse direction of said stripe is defined as X direction, said dividing step is carried out so that each of regions including identical patterns formed therein in different chips aligned in the Y direction may be aligned in the identical row of stripes, and each of regions including identical patterns formed therein in different chips aligned in the X direction may be included in the stripe in the corresponding place counted from the end place of each chip in the X direction;

b.) a step of, after having selected a stripe to be evaluated, moving a stage in the evaluation apparatus so as to bring an optical axis of said electron optical system approximately into alignment with a centerline in the X direction of one stripe;

c.) a step of continuously moving said stage in the Y direction of said one stripe;

d.) a step of scanning the pattern by an electron beam in the X direction and detecting secondary electrons emanated from points of said scanning so as to form an image of the pattern when the position of said optical axis has been aligned with one end in the Y direction of said one stripe;

e.) a step of decelerating a speed of the Y directional movement when the position of said optical axis has reached the other end in the Y direction of said one stripe to complete the image formation of said one stripe, or when it is determined that the image formation will be completed soon;

f.) a step of moving said stage in the X direction to bring the position of said optical axis approximately into alignment with a centerline of a stripe in an adjacent chip having a pattern formed therein identical to that of said one stripe for which said image has been obtained;

g.) a step of repeating a series of said steps e.) to g.); and h.) a step of confirming that all of the predetermined areas to be evaluated have been evaluated and then stopping the movement of said stage.

Thus, in the present invention, instead of comparing the patterns across the entire chips to detect the existence of the defect, the chip is divided into the stripes to obtain the image data therein, and the existence of the defect is detected as per each stripe, so that the memory for storing the image data can be made small.

Further, in one embodiment of the present invention aimed at solving the above-mentioned second problem, said electron optical system in said evaluation apparatus comprises a primary optical system for irradiating a multi-beam onto a chip and a secondary optical system for extending intervals between secondary electron groups emanated by the irradiation of respective beams, wherein a minimum interval between respective beams on the chip surface is greater than a resolution of said secondary optical system on the chip surface.

This configuration advantageously helps prevent the cross talk between the multi-beams, and allows clear images to be obtained.

Further, in another embodiment of the present invention aimed at solving the above-mentioned second problem, said evaluation apparatus has a memory sufficient to store the data of at least two stripes in one chip, and said method is characterized in further comprising a step of comparing the image data that has been obtained in the step defined in said d.) to the image data of the stripe in a different chip, which has a pattern identical with that of said one stripe, so as to detect a defect.

Accordingly, the evaluation apparatus is not required to have a large storage capacity if it only has a storage capacity sufficient to store the data of two stripes in a single chip.

Further, in still another embodiment of the present invention to solve the above-mentioned second problem, said step of selecting a stripe to be evaluated includes a step of selecting the stripe in order from an end of a chip or a step of selecting the stripe preferentially in which more defects may be expected.

Still further, in yet another embodiment of the present invention to solve the above-mentioned second problem, said multi-beam has the same distances between beams projected in the Y direction of the stripe. Owing to this configuration, occurrence of any regions of duplicated irradiation or no irradiation can be avoided.

Further, in another embodiment of the present invention, there is provided a device manufacturing method in which a wafer in the course of processing is evaluated by using the above-specified apparatus or method.

Those and other objects, features and advantages of the present invention will be apparent from the detailed description below with reference to the attached drawings illustrating preferred embodiments of the present invention by way of example only.

BRIEF DESCRIPTION OF THE DRAWINGS

FIG. 3($b$) is an enlarged view of a part "F" in FIG. 3($a$);

FIG. 6($b$) is a diagram illustrating a relationship among a positioning of a multi-beam, a width of stripe and a coordinate on a chip;

DESCRIPTION OF THE PREFERRED EMBODIMENTS

Preferred embodiments of the present invention will now be described with reference to the attached drawings.

First Embodiment

Figure 1:
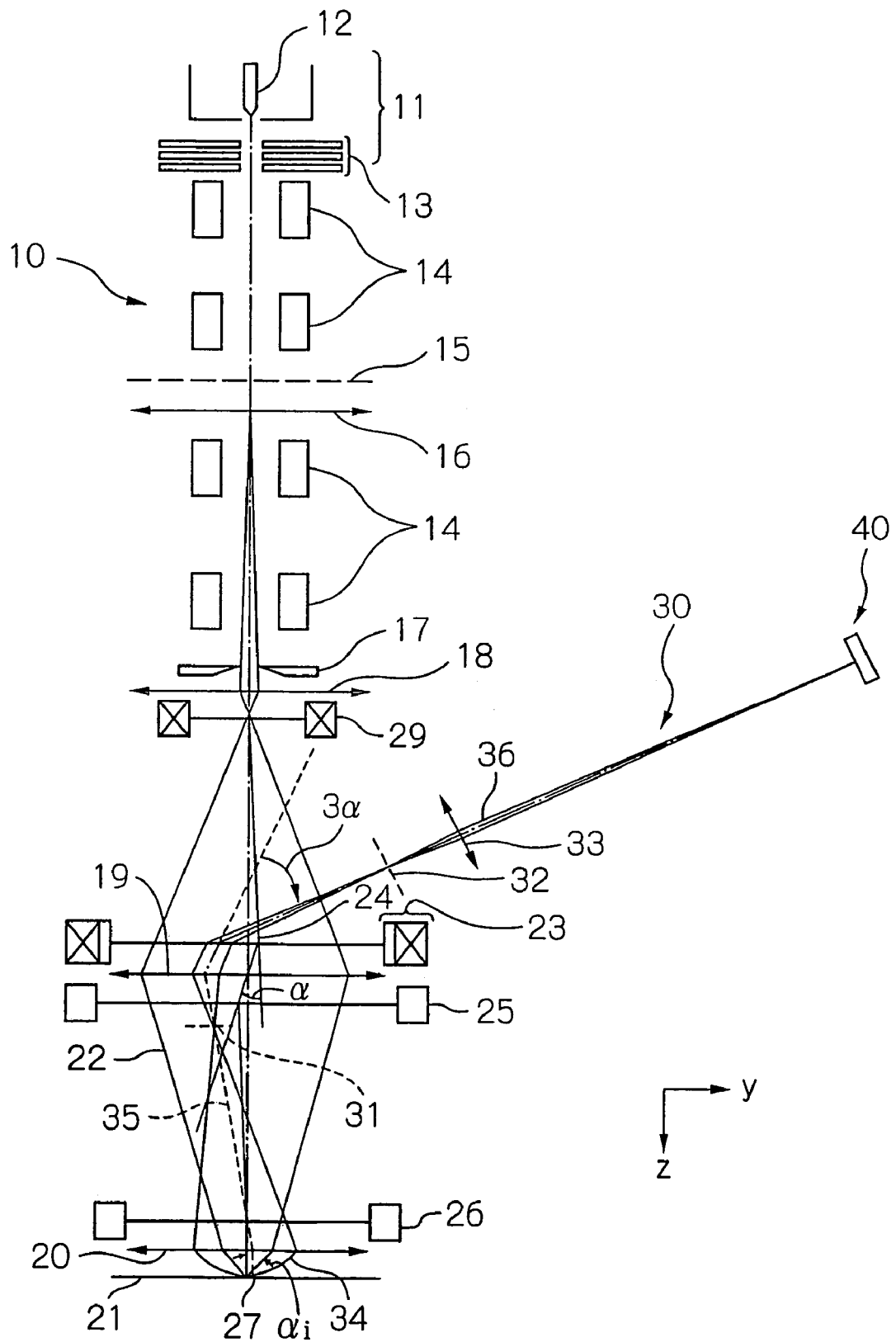
FIG. 1 is a schematic diagram showing an optical system in an electron beam apparatus according to an embodiment of the present invention.

FIG. 1 shows an electron optical system in one embodiment of the present invention, comprising a primary optical system 10, a secondary optical system 30 and a detecting system 40.

In the primary optical system, an electron gun 11 controls a LaB6 cathode 12 to be operative under a space-charge limited condition to thereby reduce a shot noise. An anode 13 is composed of three sheets of electrodes, and it can be controlled to perform a lens operation as well as to produce a high intensity condition and/or a high emittance condition by changing a voltage applied to a first anode. An axial alignment with this anode may be accomplished by shifting the cathode and the Wehnelt mechanically in the XY directions or the θ direction. Further, the axial alignment of the beam emitted from the electron gun is carried out by axial-aligning deflectors 14. A multi-aperture plate 15 is disposed in a certain range of the beam diverged from the electron gun 11, for example, within a range of angle defined by 90% intensity of the axial intensity, to separate the beams and thereby to form a multi beam. The multi-beam, having passed through the multi-aperture plate 15, is converged by a condenser lens 16 to form a crossover on a NA aperture 17. A size of the crossover is greater than the size of the NA aperture, and so it is partially trapped by the NA aperture. The multi-beam that has not been trapped by the NA aperture into an angular aperture of acceptable aberration is first reduced by a reducing lens 18, further reduced by a first objective lens 19 and a second objective lens 20 and finally focused on a sample surface. At that time, no reduced image is formed between the first objective lens 19 and the second objective lens 20, but the beams emitted through respective points in the multi-aperture plate 15 may be formed into convergent beams, parallel beams, or slightly divergent beams between those two objective lenses, as shown by reference numeral 22 (the convergent beam in the illustrated embodiment). For example, if the beams are controlled to form the slightly convergent beams, then the excitation voltage of the second objective lens 20 is decreased and resultantly the image point of the second electrons goes far away, and thereby the axial chromatic aberration of the secondary electrons is reduced, but as a result of the decreased excitation voltage, that of the primary beam increases, and in contrast, if the beams are controlled to form the slightly divergent beams, then the excitation voltage of the second objective lens 20 is increased, resulting in a relationship inverse to that described above.

Since the present invention has employed a two stage objective lens comprising the first and the second objective lenses 19, 20, as shown in FIG. 1, instead of a single stage objective lens as practiced in the prior art, to thereby reduce the excitation voltage of the second objective lens 20, the secondary electron image 31 may be formed in a position far from the objective lens 20 (the position close to the first objective lens 19 in the illustrate embodiment) to thereby allow an image 32 of the secondary electrons, which have been separated from the primary electron beam by the E×B separator 23, to be formed in a near side position of the second lens 33, so that the aperture of the lens in the secondary optical system can be made small and thereby the aberration of the secondary optical system can be reduced. Further, by forming the secondary electron image in the near side of the second lens in the secondary optical system, it is not necessary to make a distance to the image point of the magnifying lens of the secondary optical system extremely long, and thereby the length of the secondary optical system can be made shorter.

It has been confirmed by simulation that when the primary beam makes such an image forming relationship as specified above, the secondary electron image 32 is formed by the first objective lens 19 in the near side of the second lens 33 of the secondary optical system. In this case, the E×B separator 23 is disposed at a location slightly above the first objective lens 19. An electromagnetic deflector 29, referred to as a pre-E×B, is disposed immediate below the reducing lens 18, and the E×B separator 23 makes a deflection by an angle "α", so that the primary beam may pass through the center of the objective lens 19. As a result, the trajectory of the beam having been advanced along the optical axis would be the one designated by the reference numeral 24. A two stage deflector comprising respective deflectors 25 and 26 is disposed between the two objective lenses 19, 20 for scanning the sample. Although it is possible to make an axial alignment of the primary beam with respect to the second objective lens 20 by superimposing a direct current for an axial alignment over those deflectors, the present invention has employed the configuration allowing for the primary electron beam to be incident on the position 27 on the sample 21 slightly away from the optical axis, as shown in the drawing, in order to make a greater angle for separating the secondary beam from the primary beam, which will be described later. As a result, secondary electrons 34 emanated from the point slightly offset from the optical axis to the right in FIG. 1 are attracted by the electric field of the second objective lens 20 so as to be advanced in parallel with the optical axis, and then deflected by the second objective lens 20 to the left so as to move along the trajectory indicated by reference numeral 35, further deflected to the right by the first objective lens 19 and then deflected by the E×B separator 23 to the right by an angle of 3α or more so as to enter the secondary optical system 30. In this regard, the deflection angle α of the primary beam by the E×B separator 23 is a value generated from a difference between the deflection angle of 2α to the left by the electromagnetic deflector of the E×B separator and the deflection angle of α to the right by the electrostatic deflector, and this can successfully make the deflection chromatic aberration substantially zero. For example, even if the deflection angle α of the primary beam is made as small as 8°, owing to the refraction by the second objective lens 20, the refraction by the first objective lens 19 and the deflection by the E×B separator, which is enhanced by the fact that the secondary electrons have significantly lower energy than the primary electrons (for example, the primary electron beam has 500 eV of energy on the sample surface, while the secondary electron beam has only a few eV of energy), the secondary electrons 36 may be deflected by at least 30°, and this fact facilitates the designing of the secondary optical system. Further, in the illustrated embodiment, the secondary electron image 31 is formed between the second objective lens 20 and the first objective lens 19.

As described above, since the present invention has employed the two stage objective lens implemented by the objective lenses 19 and 20 so that even if the E×B separator 23 is located in a position out of conjugate point with respect to the sample, the primary beam may pass through the center of the lens, a low aberration can be achieved. Further, providing a greater angle for separating the secondary beam from the primary beam facilitates the detection of the secondary electrons.

Figure 2:
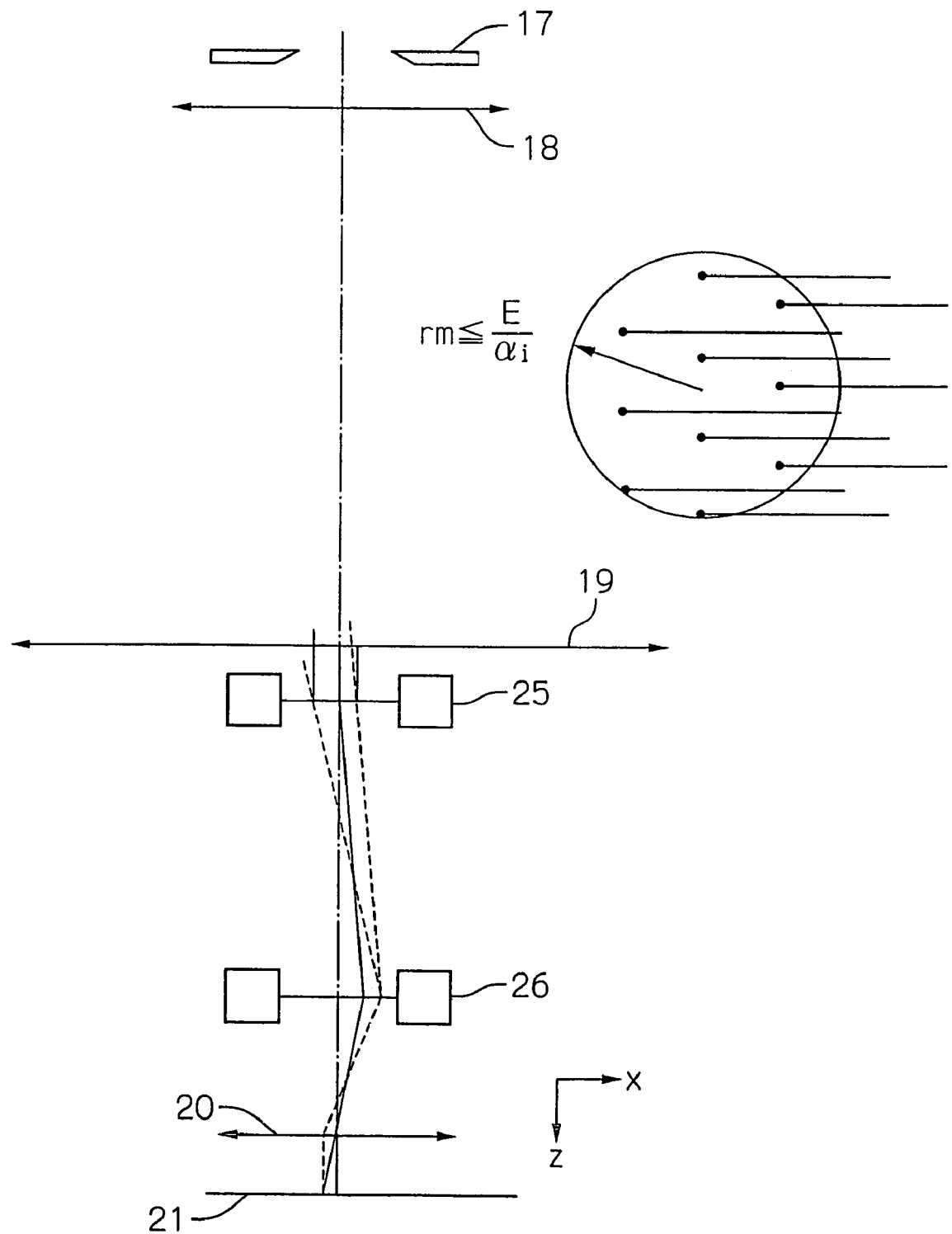
FIG. 2 is a schematic diagram showing a scanning method of the present invention along with a trajectory of a principal beam of secondary electrons in said method, wherein a positioning and scanning direction of the multi-beam is illustratively shown in an upper right circle.

FIG. 2 is a diagram showing an elevation view projected on an X-Z plane of the system of FIG. 1 taken from the perpendicular direction with respect thereto. The dotted lines indicate the trajectory of the secondary electrons during the scanning by the two scanning deflectors 25, 26 as indicated by the solid lines. That is, although the electrical scanning operation is carried in the X direction, the beam trajectory during this scanning appears as indicated by the solid line, meaning that the beam is deflected such that it can always pass through the center of the objective lens 20. The secondary electrons are deflected by the deflector 26 so as to follow either one of the trajectory defined between two dotted lines shown in the drawing.

Since the present invention employs the two deflectors 25 and 26 both implemented by the electrostatic deflectors, when the primary beam is deflected to the left by the second deflector 26, the secondary electrons are also deflected to the left, so that the secondary electrons advantageously return to the direction of the optical axis so as to enter the central region of the E×B separator 23. (If the second deflector 26 is implemented by an electromagnetic deflector, the secondary electrons are disadvantageously deflected into the direction away from the optical axis.) Further advantageously, the secondary electrons are deflected also by the first deflector 25 into the direction of the optical axis or the direction parallel to the optical axis, as illustrated in the drawing. After having entered into the secondary optical system, the secondary electrons are controlled or adjusted by a deflector (not shown) for the secondary electrons in response to the scanning operation of the primary beam so as to pass through the center of the lens, and so no problem arises.

Now, the discussion will be directed to how far from the optical axis the multi-beam having a required resolution could be positioned on the sample.

A beam convergent half-angle "$\alpha i$" (mrad) on the sample surface is determined by a condition where the aberration can meet the required specification. That is, if the beam convergent half-angle $\alpha i$ is made larger, then the aberration will increase, while if the $\alpha i$ is small, the beam current will decrease, which means that the optimal value of the $\alpha i$ may be determined by the trade-off between said two factors. A specification value of the aberration may be determined, for example, in such a manner as illustrated in FIG. 25 in the Specification of U.S. Pat. No. 6,593,152, wherein it is based on the condition to produce the maximum value of $(MTF)^2 \cdot I$, in one example, the specification value may be determined in such a manner that the beam blur level is no higher than 110 nm$\Phi$ for the condition meeting the resolution of the pattern of 100 nm.

On one hand, in addition to the intensity, an emittance "E" (mrad·μm) may be one of the most important characteristics to represent the electron beam emitted by the electron gun. In a case, by way of example, that the multi-aperture plate is disposed within a range of angle defined by 90% intensity of the axial intensity as described in the above embodiment, this emittance E may be represented by a product of a crossover diameter "d" (full width half of maximum, μm) formed by the electron gun and a divergence angle of emission $\theta$(mrad) where the intensity decreases down to 90% of the axial intensity. That is:

$$E = \theta \cdot d$$

This value of the emittance E is conserved in any Z positions on the optical axis. Therefore, if the beam convergent half-angle on the sample surface is denoted as $\alpha i$, and the radius within which the multi-beam was disposed and the 90% intensity of the axial intensity could be obtained is denoted as rm, the following formula may be obtained:

$$E = rm \cdot \alpha i$$

and this means that the multi-beam should be disposed within a circle having a radius, rm, which meets the above formula.

Further, for the determined $\alpha i$, if the beam position r is made greater, the aberration of the primary or the secondary electron beams become greater including the coma aberration, the field curvature, the astigmatism, and the transverse chromatic aberration. The r is determined such that total aberration of those kinds of aberration meet the specification values, and accordingly, the beam should be disposed within a circle defined by the radius smaller than said r and also than said rm.

An example of the positioning of the multi-beams and their scanning direction is shown in the right half of FIG. 2. Although the prior art uses fewer beams since respective beams in the multi-beams are disposed on a circle, the present invention makes it possible to increase the number of beams because each of the primary beams is positioned within a circle which satisfies the condition of $rm \leq E/\alpha i$. In this regard, although it is a matter of course that a minimum interval between beams is required to be greater than the resolution of the secondary optical system, the present invention allows more beams to be formed in the vicinity of a single optical axis within the range defined by the circle radius rm since the aberration of the secondary optical system can be made smaller.

Second Embodiment

An embodiment of a pattern evaluation method according to the present invention will now be described.

Figure 3:
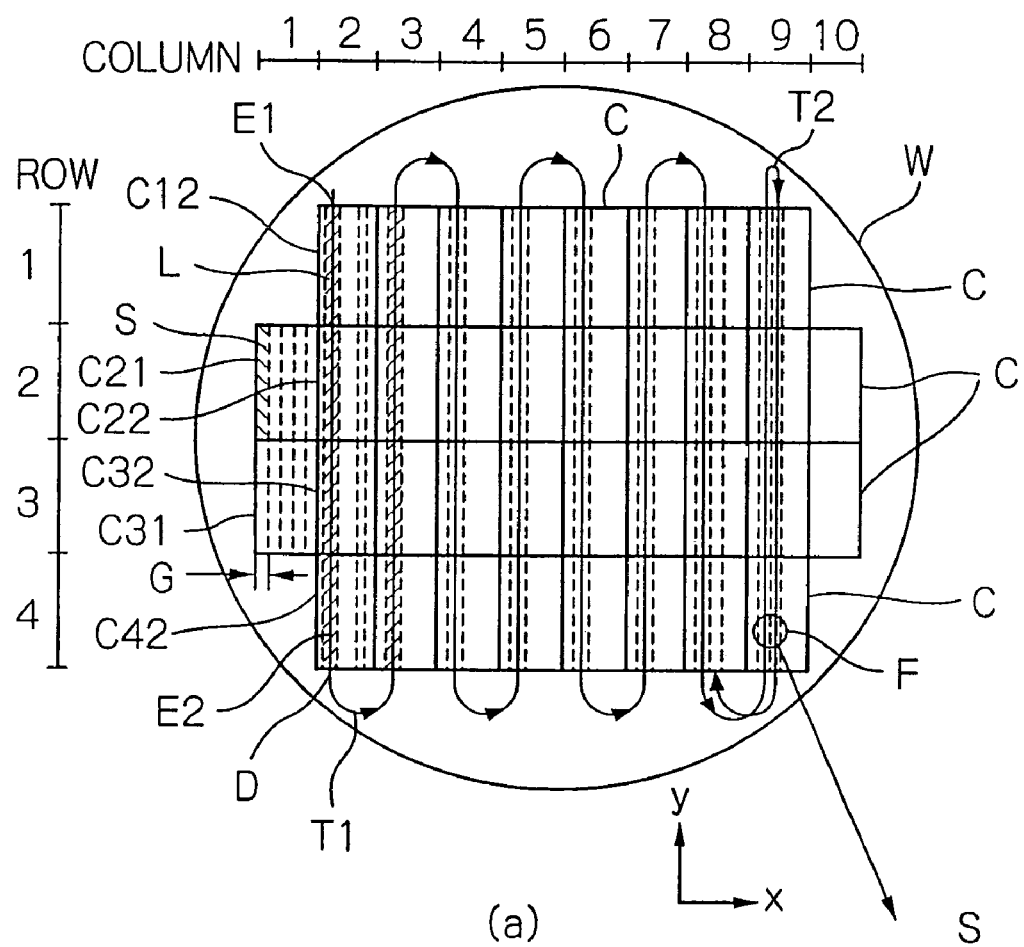
FIG. 3($a$) is a plan view illustrating a way for dividing a chip formed on a wafer, or a sample to be evaluated, into stripes in a pattern evaluation method according to the present invention.
Figure 4:
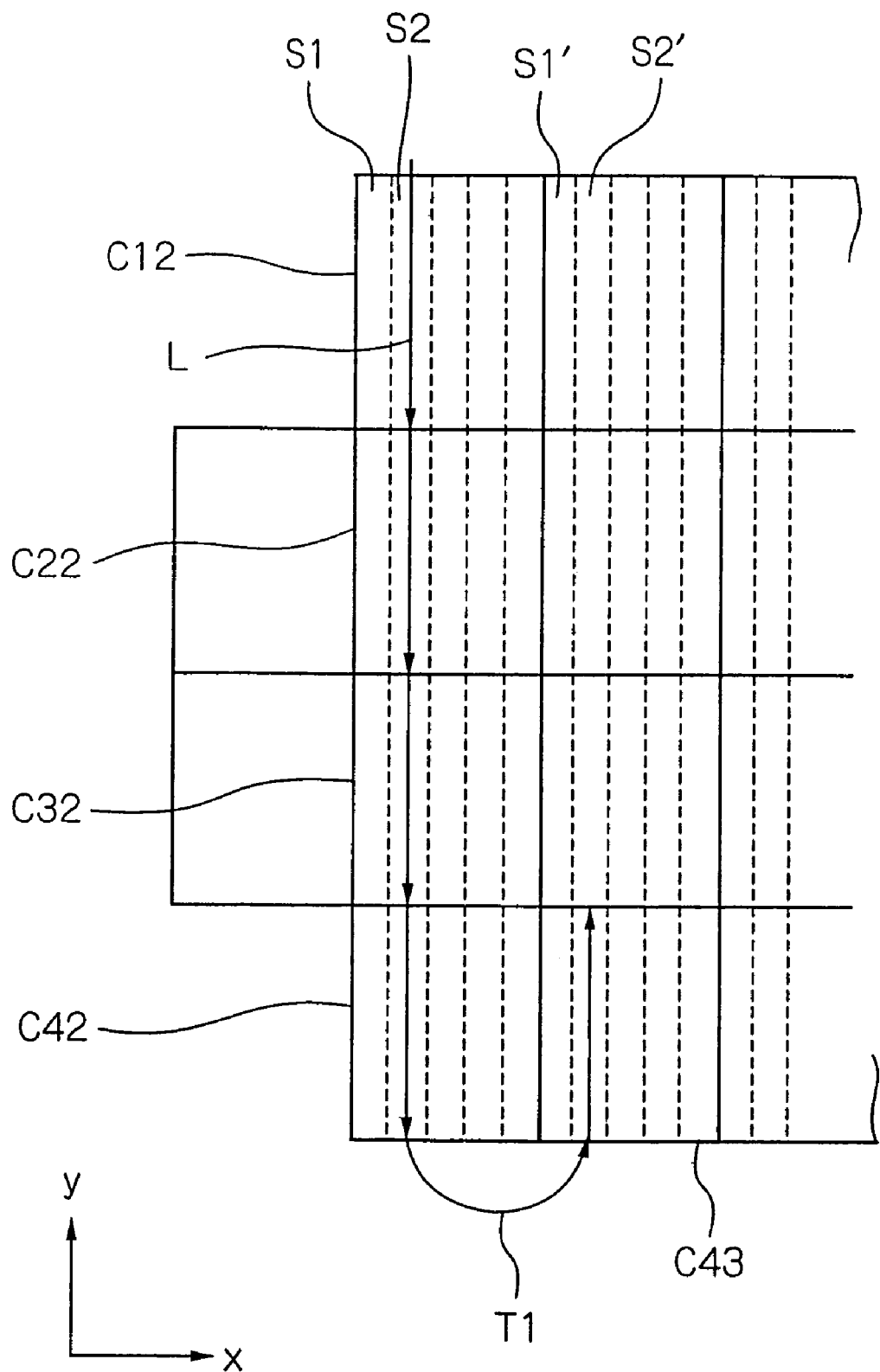
FIG. 4 is an enlarged plan view illustrating a way for dividing a chip into stripes.

FIG. 3(a) is a plan view illustrating a way for dividing a chip, or a sample, formed on a wafer into stripes and FIG. 3(b) is an enlarged view of a part designated by "F" in FIG. 3(a). Further, FIG. 4 is an enlarged plan view illustrating a way for dividing the chip into stripes.

In FIG. 3(a), the Z axis is taken in parallel to a normal line of a surface (the drawing sheet surface) of a wafer W, the X axis is taken in parallel to the sheet surface in the left and right direction, and the Y axis is taken in parallel to the sheet surface in the up and down direction. In this illustrated embodiment, a large number of chips C are formed on the wafer W almost across an entire surface thereof by 10 columns in the X direction and 4 or 2 rows in the Y direction. To simplify the description, in the drawings, a row address (1 to 4) is assigned along a longitudinal direction and a column address (1 to 10) is assigned along a laterally direction. Accordingly, taking those two chips placed in the leftmost location in the X direction as an example, starting from the top one in the Y direction, the chip located in the position defined by the second row and the first column is indicated as the chip "C21", and similarly the chip located in the position defined by the third row and the first column is indicated as the chip "C31".

The evaluation apparatus can make a scanning motion of the electron beam in the X direction by a width of field of view indicated by reference symbol "G". Every one of the chips is divided into small areas "S" (hereinafter each referred to as a stripe) each of which has a width smaller than said width "G" of the field of view and a length identical with the length of chip "C" in the Y direction.

This dividing is made to form such stripes, in which the areas on different chips having the identical patterns formed therein are arranged in the same sequence to one another, or the dividing has such an aspect that in respective chips C, those stripes defined in the same places as counted from the end in the X direction have identical patterns formed therein. For example, in FIG. 4, the areas of identical patterns formed in four respective chips aligned in the Y direction (i.e., the chip defined by the first row and the second column, C12; the chip defined by the second row and the second column, C22; the chip defined by the third row and the second column, C32; and the chip defined by the fourth row and the second column, C42) are divided to form the stripes S2 which are arranged in the same places as counted from the end in the X direction on each chip (the second places in the illustrated embodiment. Accordingly, the areas of identical patterns in the respective four chips are arranged in the same column of stripes aligned in the Y direction. Similarly for the X direction, the areas of identical patterns in the respective chips are divided to form the stripes which are arranged in the same places as counted from the end of respective chips in the X direction. Accordingly, for example, in the chip defined by the fourth row and the third column, or the chip C43, which is adjacent to the chip C42, a pattern identical with that of stripe S2 of said chip C42, is contained in the stripe S2' defined in the same count place (the second place in this embodiment) as the stripe S2 in said chip C42.

As seen from the enlarged view of a part of the stripe S in FIG. 3(b), when the entire area of the pattern is to be evaluated completely, the stripes identified as S may be slightly overlapped (by S' portion) with each other, or alternatively a gap (S'' portion) may be provided between the stripes in order to avoid the duplicated irradiation.

On the stripes of the chips, that have been divided in the manner as described above, the evaluation is now applied in the following sequence.

(1) To choose the stripe to be evaluated, a stage (not shown) is moved by the registration work so as for the optical axis P of the primary optical system of the evaluation apparatus to be positioned substantially in alignment with a central position in the X direction of the stripe in the chip to be evaluated located within an area to be evaluated on the wafer. For example, when the stripe S2 of the four chips positioned in the second columns (i.e., C12, C22, C32 and C42) is to be evaluated, firstly the stage is positioned to bring the optical axis P substantially into alignment with the center position D in the X direction of the stripe S2 (FIG. 5(a)).

Figure 5:
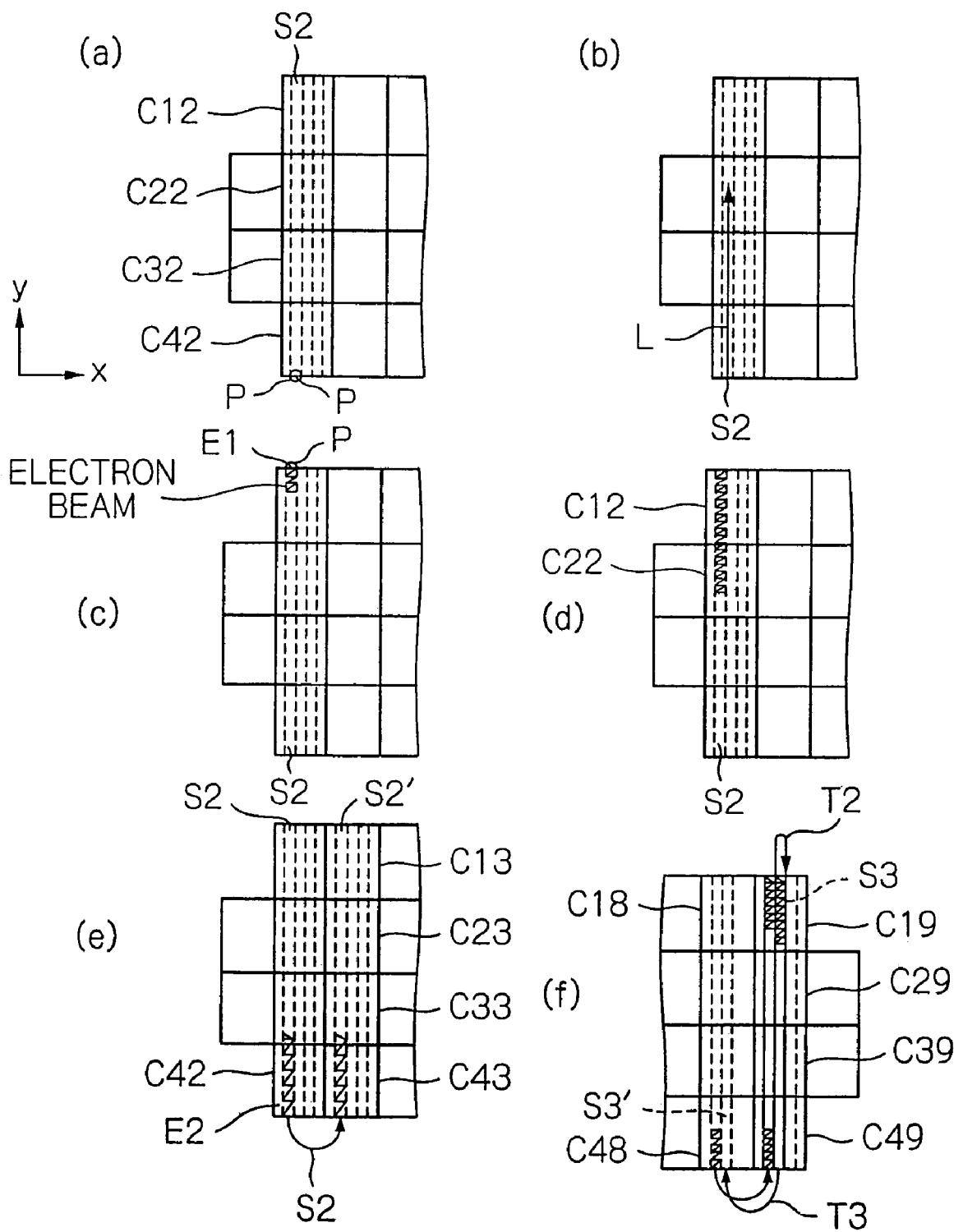
FIGS. 5($a$)–($f$) are diagrams illustrating a procedure to carry out a pattern evaluation on a chip that has been divided into stripes.

(2) Then, the stage is continuously moved in the Y direction (FIG. 5(b)) so as to allow the optical axis P to follow the trajectory designated by reference symbol L on the stripe S2.

(3) When the optical axis P has reached one end E1 of the stripe S2, the electron beam is driven in the X direction to make a scanning motion, and the secondary electrons emanated from the scanned points are detected thus to obtain the secondary image data of the pattern (FIG. 5(c)).

(4) During driving the electron beam to make the scanning motion in the X direction, the stage is continuously moved in the Y direction so as to continuously obtain the image data for the first chip C12 (FIG. 5(d) and FIG. 4). When the image data for one strip in the first chip C12 has been obtained completely, that image data is stored in a first memory (designated by reference numeral 146 in FIG. 6(a)). In this case, if the electron beam is driven to make a scanning motion in the X direction during continuously moving the stage in the Y direction, resultantly the electron beam would make a scanning motion in a slant direction across the stripe, but this may be offset by deflecting the scanning direction of the electron beam to slightly toward the Y direction (the moving direction of the stage). Therefore, substantially the electron beam would not traverse in a slant direction across the stripe.

(5) When the optical axis P has entered the second chip C22, the image data collection is started for the stripe of the chip C22, and when the optical axis P has reached the end of the chip C22, the image data for that stripe is stored in the second memory (FIG. 5(d) and FIG. 4).

(6) The pattern evaluation for the two chips is performed by comparing the image data in the first memory with the image data in the second memory. If any difference in pattern between said two chips is detected as a result of the comparison, the coordinate on which the difference has been detected and the image data on that location are stored in another or a third memory.

(7) Subsequently, the first memory is overwritten by the image data for the third chip C32 to be stored therein. It can be determined which one of said two chips has a defect by comparing the image data stored in the third memory with the image data for the chip C32 representing the corresponding location.

(8) When the optical axis P has reached to a position E2 proximal to the other end in the Y direction of the stripe S2, the stage is now decelerated (FIG. 5(e)).

(9) The stage is moved in the X direction by a distance T1 equivalent to the X directional length of one chip. Accordingly, the optical axis P of the electron optical system is moved in the X direction from the stripe S2, on which the image has been already taken, to the end of the stripe S2' of the chip in the next column (from C43 to C13) (FIG. 5(e) and FIG. 4).

(10) The stage is moved continuously in the Y direction and the similar procedures as described above from (4) to (8) are applied so as to perform the pattern evaluation on the corresponding stripes for up to the chip C19. When the series of evaluation procedure has been completed, the stage is positioned, as shown by reference symbol T2, such that the optical axis P is aligned substantially with the center position in the X direction of the stripe S3 within the same chip 19, which is to be evaluated next, and subsequently the evaluation is performed for said stripe (FIG. 5(f)).

(11) When the optical axis P has reached a position proximal to the end in the Y direction of the stripe S3 of the chip C49, the stage is decelerated, and the optical axis P is moved in the direction inverse to the X direction by the distance T3 equivalent to the X directional length of one chip to thereby bring the optical axis P into alignment with the center of the stripes S3 in the same count place on the chip C48 adjacent to the chip C49, where the evaluation of that stripe is carried out (FIG. 5(f)).

The above sequence of procedure is applied to the rest of the stripes to perform the evaluation thereof continuously.

It is to be noted that as to the first stripe on each chip (i.e., the leftmost stripe S1), since said area is defined as the peripheral circuit for the memory chip, which has a lower priority in the evaluation, therefore the evaluation may be omitted. Further, the evaluation may be omitted for the chip located in either end (i.e., C21, C31, C210, and C310). That is, in the step (1) for choosing the stripe to be evaluated, the decision may be arbitrarily made whether the stripes are sequentially selected from the end of one chip or the stripes possibly having more defects are selectively chosen.

Figure 6:
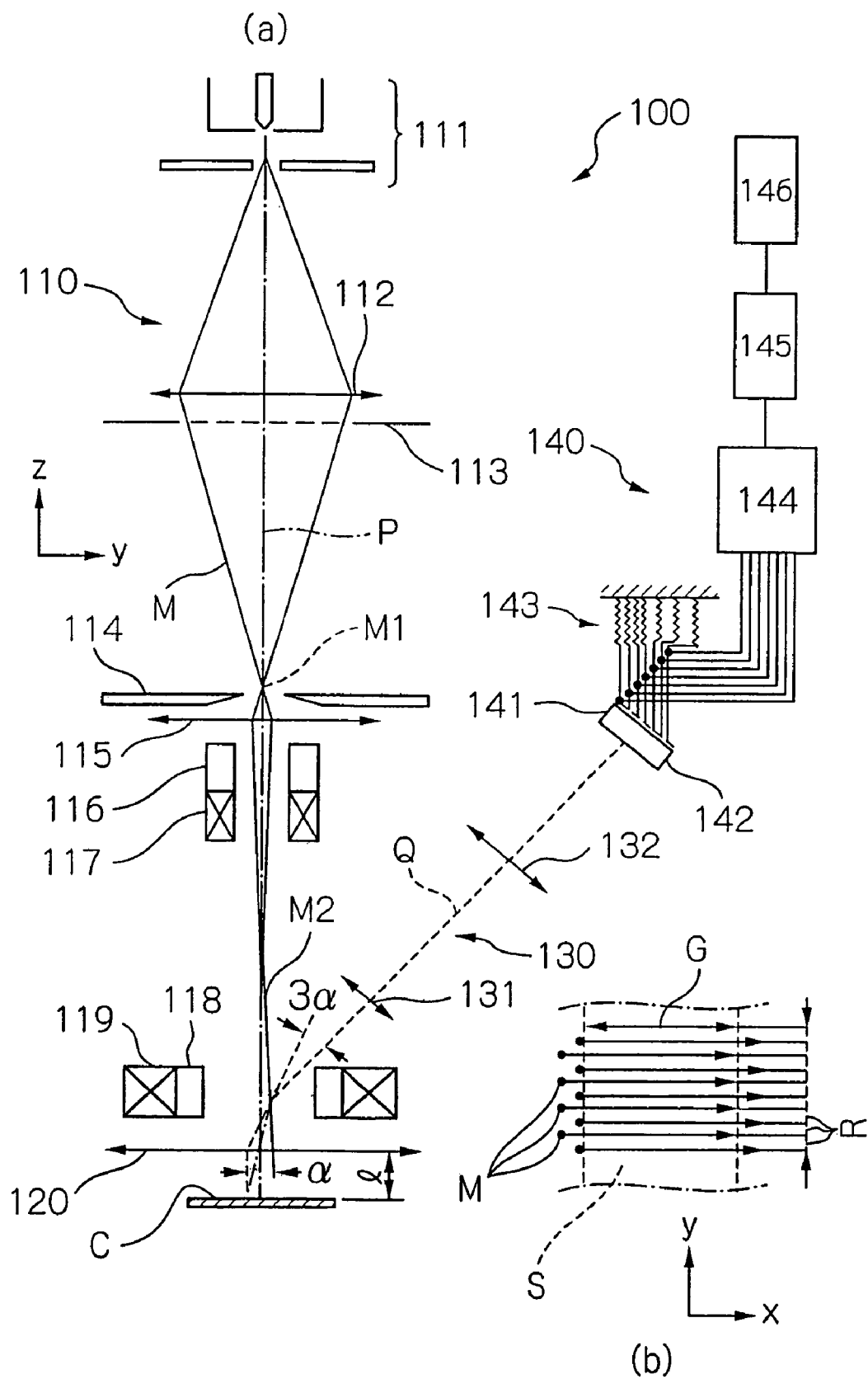
FIG. 6($a$) is a schematic diagram illustrating an example of an optical system in an evaluation apparatus that may be used in the pattern evaluation method of FIGS. 3–5.

FIG. 6(a) diagrammatically shows an evaluation apparatus 100 employing an electron beam that may be used in the pattern evaluation method according to the present invention, other than the electron beam apparatus previously shown in FIGS. 1 and 2. This apparatus 100 comprises a primary optical system 110, a secondary optical system 130 and a detector 140. The primary optical system 110 is an optical system for irradiating an electron beam onto a pattern on a chip C as a sample, which comprises: an electron gun 111 for emitting the electron beam; an electrostatic lens 112 for converging the electron beam emitted from the electron gun; an aperture plate 113 including a plurality of small through holes formed through the plate in a 2-dimensional array for shaping the electron beam into a multi-beam; a NA aperture 114; an electrostatic lens 115 for reducing the electron beam having passed through the NA aperture; an electrostatic deflector 116; an electromagnetic deflector 117; ExB separator 118, 119; and an electrostatic objective lens 120, all of these components being disposed, as illustrated in FIG. 6, with the electron gun at the topmost position in such a manner that an optical axis P of the electron beam emitted from the electron gun could be vertical to a surface of the chip C. A plurality of small through holes of the aperture plate 113 are arranged such that they are equally spaced to each other when projected in the Y direction.

The secondary optical system 130 comprises two stages of electrostatic magnifying lens 131, 132 disposed along an optical axis Q inclined from the optical axis P in the vicinity of the ExB separator 118, 119. A minimum distance between respective electron beams on the sample surface is made greater than a resolution on the sample surface for the secondary optical system.

The detector 140 comprises a micro channel plate (MCP) 141 having channels corresponding to the respective small through holes of the aperture plate 113, a multi-anode 142, a resistor 143, an A/D converter 144, an image forming circuit 145, and a memory 146.

All the above components may be those well known in the prior art, and so the detailed description of their configurations should be omitted.

An operation of the evaluation apparatus 100 having the above-mentioned configuration will now be described.

An electron beam emitted from the single electron gun 111 is converged by the electrostatic lens 112 and irradiated onto the aperture plate 113. The electron beam passes through a plurality of small through holes formed in the aperture plate 113 to be shaped into a plurality of electron beams (a multi-beam) M. The plurality of electron beams M forms a crossover M1 in the NA aperture 114. The electron beams that have formed the crossover advance toward the chip C, and are converged by the electrostatic deflector 116 and the electrostatic objective lens 120, and finally irradiated onto the chip C. The electron beams scan those divided respective stripes following the trajectory L as shown in FIG. 3(a), and in accordance with the previously explained evaluation procedure. In this case, both of the electrostatic deflector 116 and the electrostatic deflector 118 of the ExB separator are used to drive the electron beams for the scanning all at once in the X direction. As shown in FIG. 6(b), every single beam of the multi-beam scans the chip so as to cover the entire field of view G as a whole. At the same time, the electron beams are deflected by the electromagnetic deflector 117 and the ExB separator 118, 119 in the Y direction to follow the trajectory M2. At that time, since the electron beams are deflected by the electromagnetic deflector 117 to the right in the Y direction by an angle of $\alpha$, and also deflected by the ExB separator 118, 119 to the left in the Y direction by an angle of $2\alpha$, therefore they are resultantly deflected to the left in the Y direction by an angle of $\alpha$. Accordingly, the electron beams M scan a line on the chip surface defined by the coordinate in the Y direction apart from the optical axis P of the primary optical system by a distance corresponding to $\alpha \times 1$ (the distance from the principal plane of the objective lens to the surface of the chip). However, the amount of this offset from the optical axis P is so minute that it can not cause any troubles, but advantageously the electron beams that are allowed to pass through the center of the objective lens 120 contribute to reducing the aberration. By using the ExB separator in such a manner, the deflection chromatic aberration due to the ExB separator can be kept low.

Secondary electrons emanated from the chip are accelerated and converged by the accelerating electric field for the secondary electrons, which is applied between the electrostatic objective lens 120 and the chip C, and then refracted by the electrostatic objective lens 120 and further deflected by the ExB separator 118, 119 by an angle of $3\alpha$ or more. Thus, even if the value of $\alpha$ is made very small, the secondary optical system can be installed with a large angle, and accordingly the mechanical interference between the electrostatic magnifying lens 131 and the primary optical system can be avoided.

The group of secondary electrons that has been deflected by the ExB separator 118, 119 advances along the optical axis Q and is magnified by the electrostatic magnifying lenses 131, 132 to be introduced into the MCP 141. The number of electrons increases by the MCP 141 for each beam, and thus formed beams are then introduced into the anode 142, converted to the voltages by the resistor 143, and further converted to the digital signals by the A/D converter, which in turn are formed into two-dimensional images in the image forming circuit 145, and then the images between the beams of the multi-beam are connected to create the image data for one stripe of one chip, which is then stored in the memory 146. The memory 146 contains three sets of memories each prepared for one stripe of one chip, and so the memory 146 can store the images for every single stripe of three chips. It may be also possible that a difference between either two sets of image data among those three sets is calculated, and resultant difference is compared to the other one set of images, to thereby determine which one of said two sets of image data contains the defect. The image data obtained at the fourth time is stored by overwriting the oldest image data with it. Alternatively, if only the difference in the image data between the two sets of memories is stored in another small memory, then three sets of memories can be reduced to two sets of memories.

FIG. 6(b) shows a relationship among the positioning of the multi-beam on the chip, the width of the stripe and the coordinates. In this drawing, the intervals R between adjacent beams M when they are projected on the Y axis are all equal and those beams are controlled to scan the stripe in the X direction so as to cover the entire stripe as a whole, while at the same time, the stage is continuously moved in the Y direction.

In a different embodiment from the one above, the image data for one stripe in the first chip to be evaluated may be stored in the memory, and the subsequent image data may be always compared to said stored image data. In this case, the memory can be further reduced in its capacity.

Figure 7:
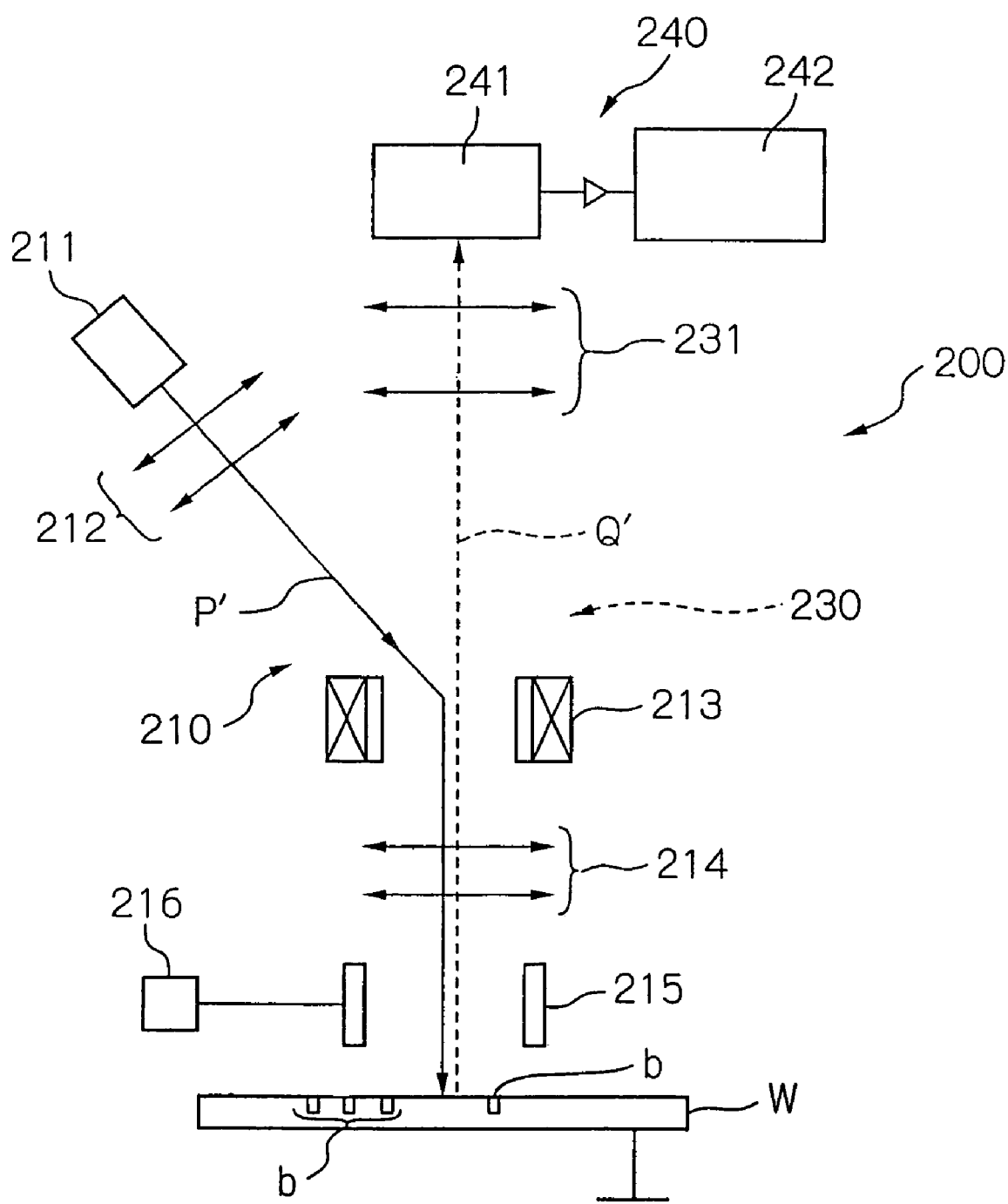
FIG. 7 is a schematic diagram showing another embodiment of an evaluation apparatus that may be used in the pattern evaluation method of FIGS. 3–5.

FIG. 7 diagrammatically shows another embodiment of an evaluation apparatus employing an electron beam that may be used in the pattern evaluation method according to the present invention.

This evaluation apparatus 200 comprises: a primary optical system 210 for shaping an electron beam emitted from an electron gun into a predetermined shape (e.g., a rectangular or linear shape) and irradiating thus shaped electron beam onto a surface of a sample to be inspected (i.e., a wafer W or a chip C); a secondary optical system 230 for irradiating secondary electrons emanated from the wafer or the like onto a detector; and a detecting system 240 for receiving the secondary electrons and forming an image for a pattern on the chip.

The primary optical system 210 comprises an electron gun 211 for emitting an electron beam, a two stage electrostatic lens 212 for converging the electron beam, an ExB separator 213, a two stage electrostatic objective lens 214, and an axially symmetrical electrode 215 with its own power supply 216, all of these components being disposed as shown in FIG. 7 sequentially along an optical axis P' having a certain angle relative to the direction normal to the wafer surface with the electron gun 211 at the topmost location.

The secondary optical system 230 is disposed along an optical axis Q' of the secondary electrons from a chip C in the direction normal to a surface of a wafer and comprises a two stage electrostatic lens 231.

The detecting system 240 comprises a detector 241 and an image forming circuit 242.

In the above configuration, the electron beam emitted from the electron gun 211 is converged and shaped into a predetermined shape by the electrostatic lens 212, deflected by the E×B separator 213 into a direction vertical to the wafer and finally irradiated on the wafer by the two stage electrostatic objective lens 214. The wafer contains a via "b" embedded therein, and, specifically for a discharge-prone wafer, an electric field to be applied to the wafer may be weakened by applying a voltage to an axially symmetrical electrode 215 from a power supply 216. Secondary electrons emanated from the wafer W pass through the electrostatic objective lens 214, enter the secondary optical system 230, and further pass through the electrostatic magnifying lens 231 to be formed into an image on the detector 241 in the detecting system 240. The secondary electrons that have been formed into the image in the detector 241 are then formed into a two-dimensional image by the image forming circuit 242.

Third Embodiment

Figure 8:
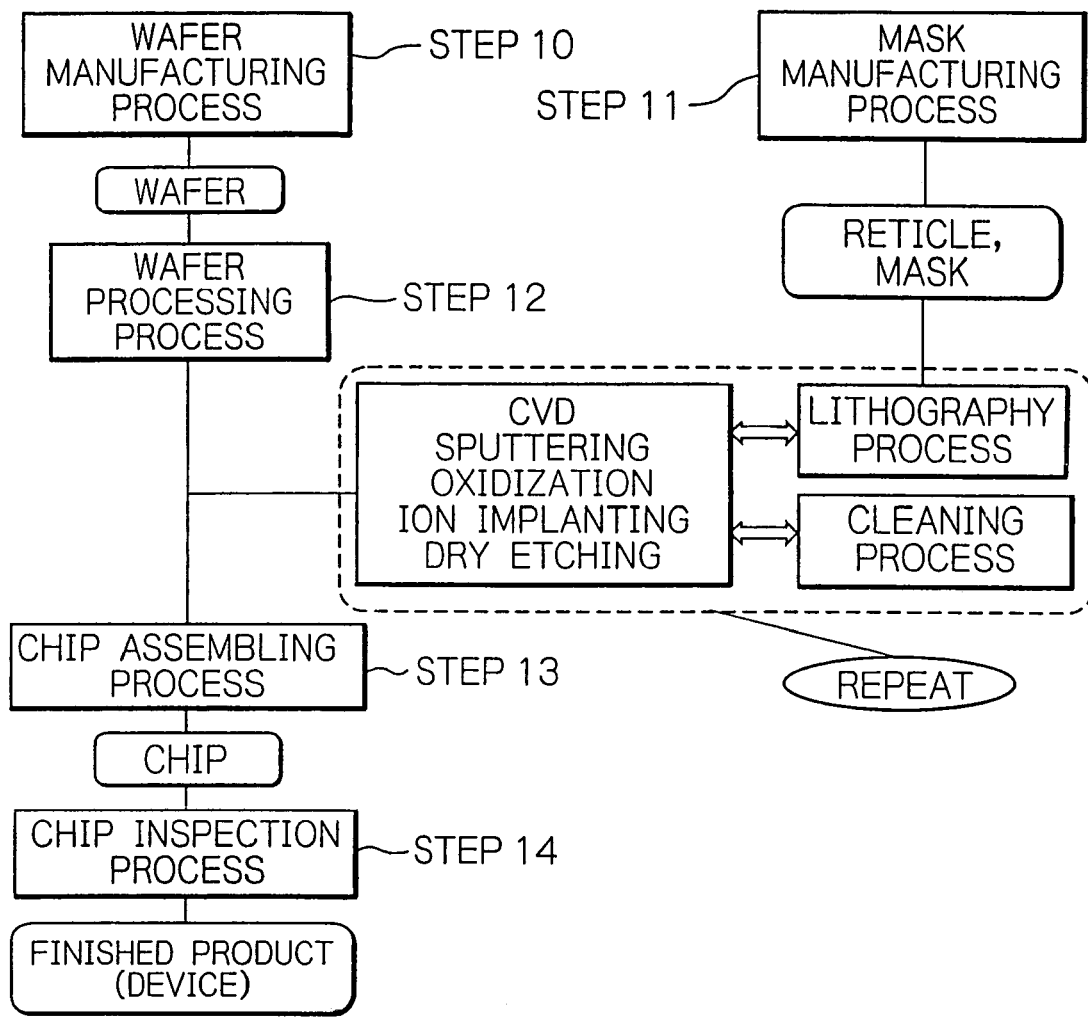
FIG. 8 is a flowchart showing a semiconductor device manufacturing process.

FIG. 8 is a flow chart representing a way for applying the electron beam apparatuses or the pattern evaluation methods, which have been described in the above embodiments, to the evaluation of a wafer in a semiconductor device manufacturing process.

An example of the device manufacturing process will now be described with reference to a flow chart of FIG. 8.

The manufacturing process includes the following main processes.

(1) A wafer manufacturing process for manufacturing a wafer (or wafer preparing process for preparing a wafer). (Step 10)

(2) A mask manufacturing process for fabricating a mask to be used in the exposure (or a mask preparing process). (Step 11)

(3) A wafer processing process for performing any processing treatments necessary for the wafer. (Step 12)

(4) A chip assembling process for cutting out those chips formed on the wafer one by one to make them operative. (Step 13)

(5) A chip inspection process for inspecting an assembled chip. (Step 14)

It is to be appreciated that each of those processes further comprises several sub-processes.

Among those main processes, the main process that gives a critical affection to the performance of the semiconductor device is the wafer processing process. In this wafer processing process, the designed circuit patterns are stacked on the wafer one on another, thus to form many chips, which will function as memories and MPUs. This wafer processing process includes the following sub-processes.

(1) A thin film deposition process for forming a dielectric thin film to be used as an insulation layer, a metallic thin film to be formed into a wiring section or an electrode section, or the like (by using the CVD or the sputtering).

(2) An oxidizing process for oxidizing the formed thin film and or the wafer substrate.

(3) A lithography process for forming a pattern of the resist by using a mask (reticle) in order to selectively process the thin film layer and/or the wafer substrate.

(4) An etching process for processing the thin film layer and/or the wafer substrate in accordance with the pattern of the resist (by using, for example, the dry etching technique).

(5) An ions/impurities implant and diffusion process.

(6) A resist stripping process.

(7) An inspection process for inspecting the processed wafer.

It is to be noted that the wafer processing should be performed repeatedly as desired depending on the number of layers, thus to manufacture a semiconductor device that will be able to operate as designed.

Figure 9:
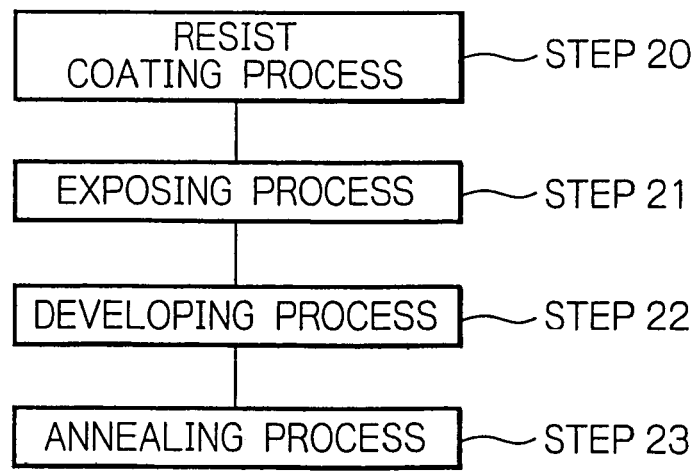
FIG. 9 is a flow chart showing a lithography process of the semiconductor device manufacturing process of FIG. 8.
Figure 10:
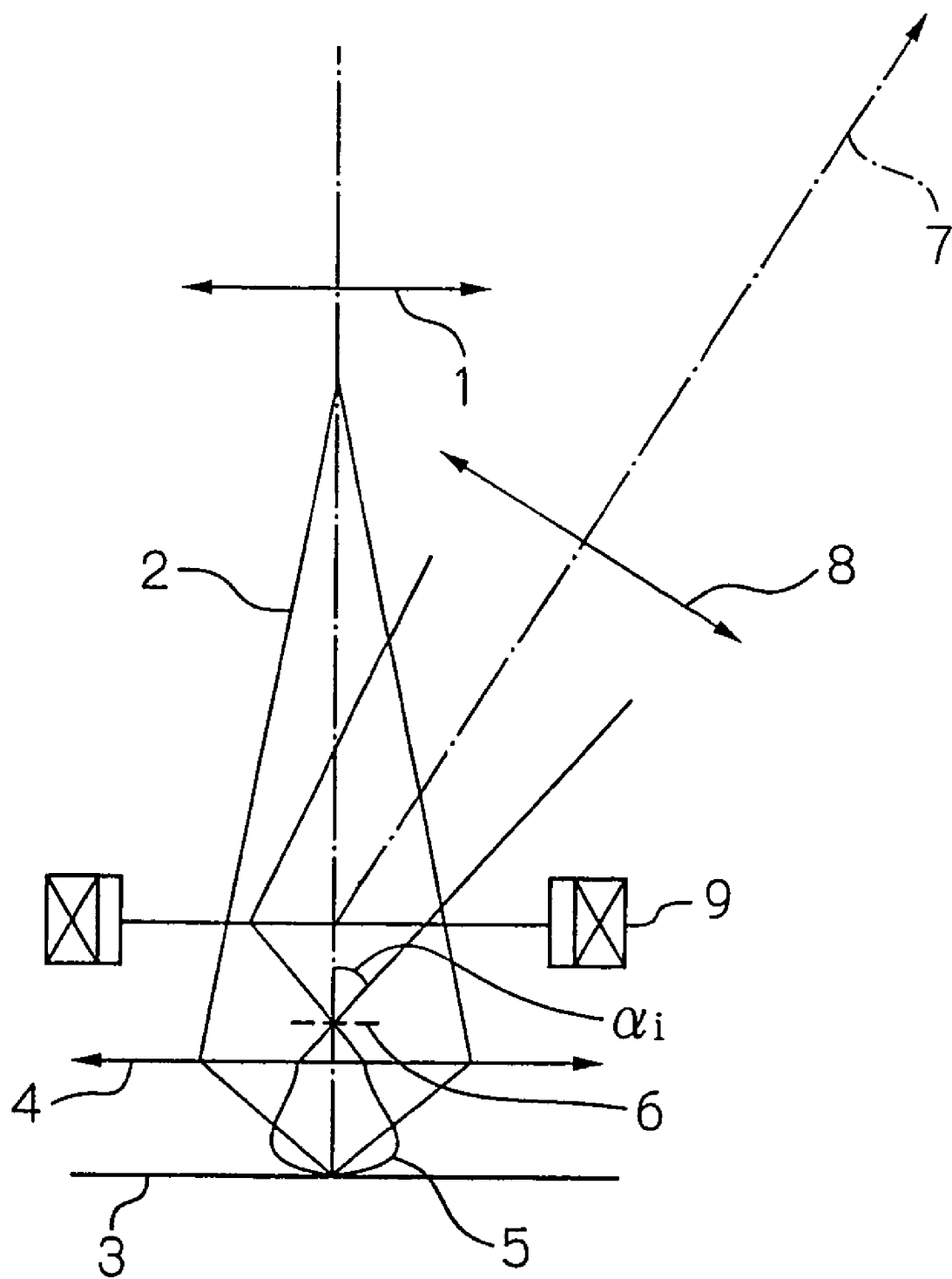
FIG. 10 is a schematic diagram showing an optical system in an electron beam apparatus according to the prior art.

FIG. 9 is a flow chart illustrating the lithography process included as a core process in said wafer processing process. The lithography process comprises the respective processes as described below.

(1) A resist coating process for coating the wafer having a circuit pattern formed thereon in the preceding stage with the resist. (Step 20)

(2) An exposing process for exposing the resist. (Step 21)

(3) A developing process for developing the exposed resist to obtain the pattern of the resist. (Step 22)

(4) An annealing process for stabilizing the developed pattern. (Step 23)

Known procedures may be applied to all of the semiconductor manufacturing process, the wafer processing process, and the lithography process described above.

When the electron beam apparatus or the pattern evaluation method according to the above-described respective embodiments is applied to the wafer inspection process (7) described above, a highly precise inspection can be accomplished without any faults in the secondary electron image, even for a semiconductor device having a micro-fine pattern, thus improving the yield of the products and prohibiting any defective products from being delivered.

It is to be noted that the pattern evaluation according to the present invention is applicable to a broad range of pattern evaluations, including a defect inspection, a line width measurement, an aligning precision evaluation, a potential contrast measurement and so on, for a sample such as a photo mask, a reticle, a wafer and the like.

As described above, according to the present invention, since a large number of multi-beams can be formed around a single optical axis, the pattern evaluation can be performed with high throughput, and further, since only a single electron optical lens column is necessary, the unit can be manufactured at low cost.

Further, according to the present invention, since in all the chips, the regions having the identical patterns formed therein are divided into stripes, and the stripe to be evaluated is chosen and then the evaluation is performed on that stripe, the capacity of the memory for storing the image data may be reduced.

Furthermore, since a plurality of electron beams is used in the pattern evaluation, the throughput can be improved.

What is claimed is:

1. A pattern evaluation method for evaluating patterns formed on a sample, comprising:
   a) a step of advancing an electron beam emitted from an electron gun along a primary optical system formed normal to the sample;
   b) a step of deflecting said electron beam toward a beam separator by a deflector;

c) a step of deflecting said electron beam by an angle of α to one direction by an electrostatic deflector of said beam separator and further deflecting said electron beam by an angle of 2α a to the opposite direction by an electromagnetic deflector of said beam separator whereby said electron beam is resultantly deflected to the opposite direction by an angle of α as a difference between said two deflections;

d) a step of focusing said primary beam on said sample by an objective lens;

e) a step of deflecting secondary electrons emanated from said sample to detectors by said beam separator after having passed through said objective lens; and f) detecting said secondary electrons by said detectors and evaluating a sample image.

2. A pattern evaluation method in accordance with claim 1, in which said primary beam comprises a plurality of electron beams positioned within a circle which has a predetermined radius from an optical axis of said primary optical system.

3. A pattern evaluating method in accordance with claim 1, in which said primary electron beam is scanned on said sample by a deflecting system which has at least an electrostatic deflector as a final step deflector.

4. A pattern evaluation method comprising;
a) a step of emitting an electron beam from an electron gun having a single emission area;
b) a step of forming multi-beams by irradiating said electron beam into multi-apertures;
c) a step of focusing said multi-beams on said sample and scanning said sample thereby;
d) a step of deflecting secondary electrons emanated from points of scanning on said sample toward detectors by a beam separator; and
e) evaluating a pattern on said sample by signals detected by said detectors;
wherein said multi-beams are positioned within a circle having a radius determined from a convergent half-angle α i on a sample and an emittance E of said electron gun.

5. A pattern evaluation method in accordance with claim 4, wherein said radius rm satisfies the condition of $rm < E/\alpha i.$ 6. A pattern evaluation method for evaluating a pattern formed on a sample, comprising:
a.) a step of irradiating an electron beam emitted from an electron gun onto a plurality of apertures;
b.) a step of reducing electron beams, which have been separated through said apertures, in two or more stages, so as to focus them on a sample and scanning said sample by said reduced electron beams;
c.) a step of extending intervals of secondary electrons, which have been emanated from points of scanning on said sample, by an objective lens and separating said secondary electrons from a primary optical system by a beam separator; and
d.) a step of detecting said separated secondary electrons by secondary electron detectors,
said method characterized in that:
the second step of reducing in said stage of reducing the aperture image is carried out by an objective lens, and a first enlarged image of the secondary electron is formed in a location behind said beam separator.

7. A pattern evaluation method for evaluating a pattern formed on a sample, comprising:
a.) a step of reducing electron beams, which have passed through a plurality of apertures and scanning a sample by said electron beams;
b.) a step of extending distances between secondary electrons, which have been emanated from points of scanning on said sample, by an objective lens;
c.) a step of separating said secondary electrons, after having passed through said first lens, from a first optical system by a beam separator;
d.) a step of extending distances between said secondary electrons, after having separated from said primary optical system, by a lens;
e.) a step of detecting a plurality of secondary electron groups independently by secondary electron detectors; and
f.) a step of forming an image by using said detected signals and performing a pattern evaluation, said method characterized in that:
said plurality of electron beams are positioned within a circle having a radius determined such that an aberration in the primary optical system is controlled to be equal or less than a predetermined value.

8. A pattern evaluation method in accordance with claim 4, in which said emittance E is represented by product of a crossover diameter d formed by the electron gun and a divergence angle of emission θ where the intensity decreases down to 90% of the axial intensity.

9. A pattern evaluation method in accordance with claim 6, in which an electric field applied between said sample and said objective lens is weakened when a discharge-prone sample is evaluated.

10. A pattern evaluation method for evaluating a pattern formed on a sample, comprising:
a.) a step of reducing electron beams, which have passed through a plurality of apertures and scanning a sample by said electron beams;
b.) a step of extending distances between secondary electrons, which have been emanated form points of scanning on said sample, by an objective lens;
c.) a step of separating said secondary electrons, after having passed through said first lens, from a first optical system by an beam separator;
d.) a step of extending distances between said secondary electrons, after having separated from said primary optical system, by a lens;
e.) a step of detecting a plurality of secondary electron groups independently by secondary electron detectors; and
f.) a step of forming an image by using said detected signals and performing a pattern evaluation, said method characterized in that;
said plurality of electron beams are positioned within a circle having a radius determined such that an aberration in the secondary optical system is controlled to be equal or less than a predetermined value.

* * * * *